United States Patent [19]

Whitwam et al.

[11] Patent Number: 4,644,947
[45] Date of Patent: Feb. 24, 1987

[54] RESPIRATOR

[76] Inventors: James G. Whitwam, Flat A, 47 Beaumont Street, London W1; Mihir K. Chakrabarti, 19 Elton Avenue, Greenford, both of England

[21] Appl. No.: 762,294

[22] Filed: Aug. 5, 1985

Related U.S. Application Data

[63] Continuation-in-part of Ser. No. 484,339, Apr. 12, 1983, Pat. No. 4,596,247.

[30] Foreign Application Priority Data

Apr. 15, 1982 [GB] United Kingdom ............... 8210912

[51] Int. Cl.[4] ............................................. A61M 16/00
[52] U.S. Cl. ............................ 128/204.25; 128/207.16
[58] Field of Search .................... 128/204.18, 204.24, 128/204.25, 205.13, 205.24, 205.14, 205.15, 205.16, 911, 204.23, 207.14, 207.15, 207.16

[56] References Cited

U.S. PATENT DOCUMENTS

| | | | |
|---|---|---|---|
| 2,918,917 | 12/1959 | Emerson | 128/204.21 |
| 3,485,243 | 12/1969 | Bird et al. | 128/204.25 |
| 3,993,059 | 11/1976 | Sjostrand | 128/205.24 |
| 4,030,492 | 6/1977 | Simbruner | 128/205.24 |
| 4,067,328 | 1/1978 | Manley | 128/205.24 |
| 4,265,237 | 5/1981 | Schwanbom et al. | 128/204.25 |
| 4,351,329 | 9/1982 | Ellestad et al. | 128/205.24 |
| 4,457,304 | 7/1984 | Molnar et al. | 128/204.25 |
| 4,463,755 | 8/1984 | Suzuki | 128/911 |
| 4,463,756 | 8/1984 | Thuc | 128/204.24 |
| 4,519,388 | 5/1985 | Schwanbom et al. | 128/207.15 |
| 4,543,951 | 10/1985 | Phuc | 128/204.25 |

FOREIGN PATENT DOCUMENTS 75542 3/1983 European Pat. Off. ....... 128/207.15

| | | | |
|---|---|---|---|
| 82/03014 | 9/1982 | World Int. Prop. O. | |
| 1488317 | 10/1977 | United Kingdom | 128/204.25 |
| 1585091 | 2/1981 | United Kingdom | |
| 2057273 | 4/1981 | United Kingdom | |

Primary Examiner—Henry J. Recla
Attorney, Agent, or Firm—Marshall, O'Toole, Gerstein, Murray & Bicknell

[57] ABSTRACT

A respirator for use in replacing or assisting the respiratory function in patients in whom spontaneous respiration is either absent or insufficient is described. The respirator includes a respirator conduit having a downstream end which is attachable to a proximal end of a patient tube 3. A respiratory gas line 6 is connected to a downstream section of the conduit and opens into the conduit at a first location adjacent but upstream of the downstream end 4. An axially extending driving gas jet nozzle 11 is provided at a location which is at least one tidal volume upstream from the patient attachment 4, where the respiratory fresh gas is supplied. The driving gas from the driving jet 11 simply controls the tidal volume like a pneumatic piston and drives the respiratory gas accumulated in the conduit 5 from the supply of the continuous flow of the respiratory gas. The driving gas from jet 11 does not take part in the pulmonary gas exchange. Ventilation of any patient at any frequency and tidal volume is possible with this new respirator, safely, with any chosen low pressure conditioned and humidified respiratory gas including volatile anaesthetic vapors.

In its simplest form the respirator can be described as a slave driving jet placed in the wide tube of a T piece, one tidal volume distal to the patient attachment where the respiratory gas is supplied through the narrow limb of the T-piece.

2 Claims, 8 Drawing Figures

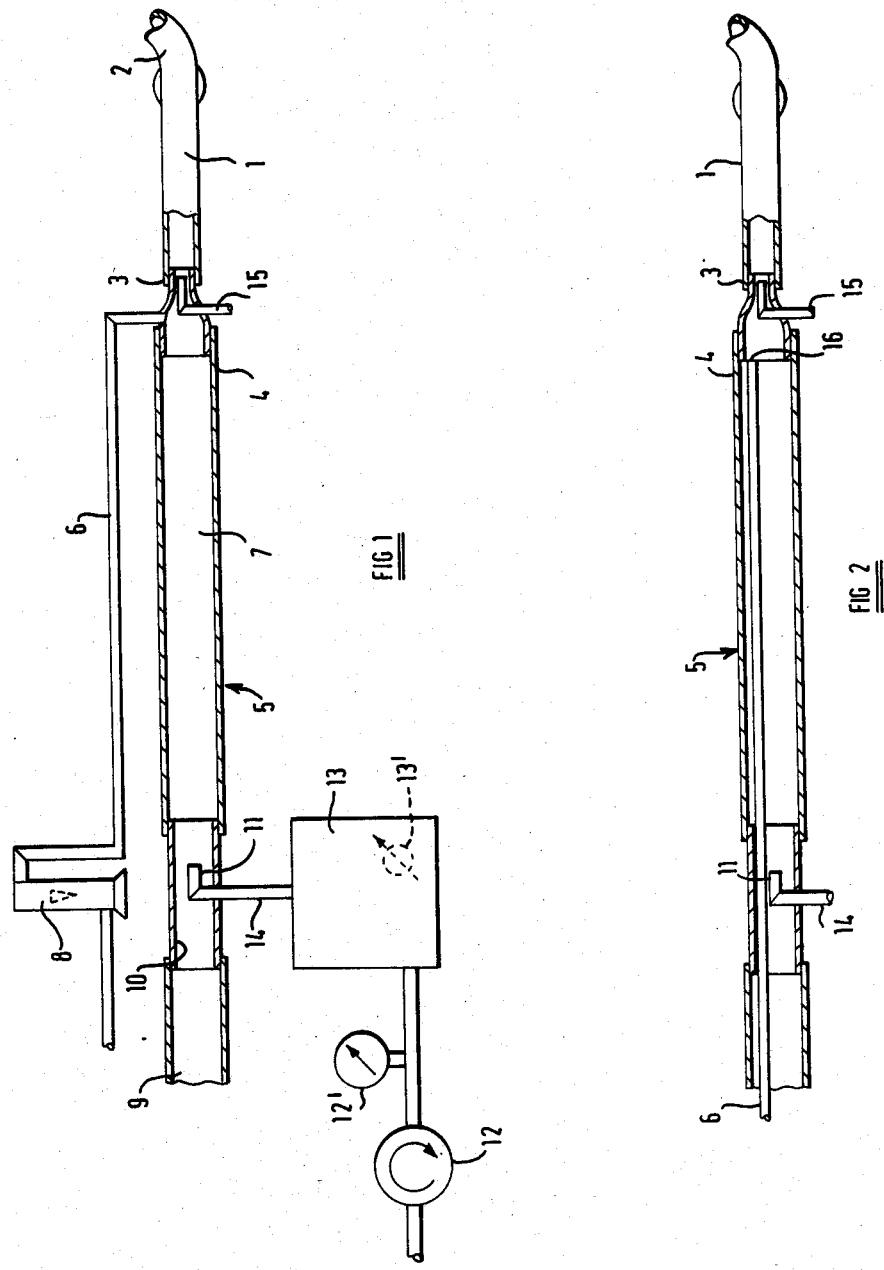

RESPIRATOR

CROSS REFERENCE TO RELATED APPLICANTS

This Application is a continuation-in-part of application Ser. No. 06/484,339 filed Apr. 12, 1983. Now U.S. Pat. No. 4,596,247.

BACKGROUND OF THE INVENTION

This invention relates to a respirator for use in replacing or assisting the respiratory function in patients in whom spontaneous respiration is either absent or insufficient. Such respirators are used in surgery and anaesthesia, in critical care and respiratory therapy units for resuscitation, and in the general nursing of patients, including infants, whose natural respiratory activity is inadequate. Respirators of this kind are sometimes also termed ventilators.

One known form of respirator is designed to deliver a respiratory gas volume to the lungs intermittently through an inlet tube of large (i.e. 2.5 cm) internal bore via an inspiratory valve, the expired gas being allowed to be discharged from the lungs through a similar outlet tube via an expiratory valve. The inspiratory circuit may contain a humidification device. The inlet and outlet tubes of the respirator are connected via a Y-piece to the patient duct, i.e. any attachment to the patient which delivers gas to the patient, such as an endotracheal tube, a mask, or a tracheostomy tube. The inlet and outlet tubes have a large bore to minimise resistance in the circuit.

The operation of the known respirators of this first kind is controlled in accordance with predetermined input parameters. In a so-called pressure-controlled respirator, respiratory gas under pressure is supplied to the patient and the inlet valve interrupts the supply of respiratory gas and the outlet valve is opened when a specific predetermined pressure has been built up in the patient duct. In a so-called volumetrically controlled system, a measured quantity of the respiratory gas is supplied to the patient via a nonreturn inlet valve and the outlet valve is controlled to connect the patient duct to atmosphere once the supply of respiratory gas has taken place. Respirators of this kind commonly have a safety valve in the inhalation line to relieve any excess pressure.

Various sophisticated control systems have been developed for use with these known respirators to improve their adaptation to the instantaneous physiological condition of the patient.

Whilst these control systems have improved the adaptation and safety of the respirators, the adaptation to the patient is still far from ideal and the intervention of a skilled human operator is vital to ensure adequate adaptation of the respirator to significant changes in the patient's condition. Especially when a patient is in a recovery situation, a complicated sensing and triggering system is required to synchronise the operation of the respirator with the patient's own spontaneous breathing effort. Even this system fails if the patient's respiratory frequency is high. Further, reversal of a patient from the effects of paralysing drugs, a change to manual respirator operation or a changeover to continuous positive airway pressure (CPAP) requires disconnection of the respirator.

Because of the large internal volume of the tubing and humidifier, the known respirators of this kind for use with adults are not suitable for children or babies.

A further drawback of the known respirators under discussion is that their complexity and size preclude them being used in situations where portability is required. This complexity also means that significant effort may be required in maintaining the respirator at peak operating efficiency and in keeping the respirator in a clean condition. The complexity of these respirators both in manufacture and operation naturally mean that they are high cost items of equipment requiring expensive and skilled operators for safe use.

When the thoracic compliance of a patient is low, the known ventilators generate at normal respiratory rates high pressures in the lungs which may cause damage. To avoid such pressures, a higher frequency with smaller tidal volumes is desirable. The known ventilators of this first kind are unsuitable for this purpose because of their large internal compressible volumes.

In an attempt to overcome this problem, a second known form of respirator, the so-called jet respirator, has been developed. In a jet respirator, a proximal end of the patient duct is open to atmosphere and the respiratory gas is supplied to the patient duct as a high pressure jet through a nozzle inserted into the open proximal end of the patient duct. Jet respirators are however of limited application.

While this second form of respirator shares many of the disadvantages of the first kind of respirator discussed above, it has advantages in certain applications and has a particular advantage of employing no valves in the patient circuit, so that spontaneous respiration by the patient in a recovery situation is facilitated.

In known jet respirators, the high pressure respiratory gas is delivered in pulses which determine the inhalation phase of respiration, the exhalation phase occurring between pulses with the exhaled air passing to atmosphere through the open proximal end of the patient duct around the respiratory gas nozzle. The frequency of breathing and hence the minute volume can be varied by varying the frequency of the pulses of respiratory gas, although this adjustment is not quite as simple as appears at first and other settings may require compensating changes because of the high pressure condition of the respiratory gas in order to maintain a desired composition of the respiratory gas. Further, variation of the composition of the respiratory gas and the introduction of the anaesthetic gases, when required, is complicated by the fact that the respiratory gas is at high pressure.

As a result of the open proximal end of the patient duct, the high pressure respiratory gas tends either to leak out or to entrain atmospheric air and this is a further complication which has to be taken into account in adjusting the concentration of the constituent gases of the respiratory gas and the introduction of anaesthetic gases into the respiratory gas. The use of high pressure respiratory gas also presupposes the availability of all the required gases under pressure and, although this will commonly be the case in large medical establishments, it does place a considerable limitation on the environment in which the jet respirator can be used. Another limitation is imposed by the fact that it may not always be possible to supply the required minute volume of respiratory gas under all circumstances.

Because of its construction the jet respirator has the undesirable feature of being noisy in operation and may also cause trauma due to vibration of the patient duct in the patient's airway.

OBJECT OF THE INVENTION

It is an object of the present invention to overcome at least some of the problems of known respirators and to provide a respirator which is of simple construction and low cost, yet is versatile, adaptable to the patients age and condition and reliable and safe in operation.

SUMMARY OF THE INVENTION

Accordingly, the present invention provides a respirator including a respirator conduit 5 having a downstream end for connection to a patient duct 1; supplying means for supplying relatively low pressure respiratory gas 6 to a patient from a first location 4; means for introducing and directing pulses of driving gas with driving jet 11, axially of and in the respirator conduit towards the downstream end of the respirator conduit from a second location 11, at least one tidal volume upstream of the first location 4 to drive respiratory gas supplied by the supplying means into a patient's lungs; and means for supplying a constant stream of driving gas 17 to the respirator conduit for operation with a desired end expiratory pressure.

In a second aspect, the present invention provides a method of ventilating a patient, comprising: inserting one end of a patient duct 1 into the mouth of the patient; continuously supplying relatively low pressure respiratory gas to the patient from a first location 4; introducing pulses of driving gas into a respirator conduit 11 and driving the same from a second location at least one tidal volume upstream of the first location toward a downstream end of the respirator conduit connected to the patient duct to drive the respiratory gas into the patient's lungs.

In a third aspect, the present invention provides a method of ventilating a patient, which method comprises: inserting one end of a patient duct into a patient's mouth, the other end of the patient duct being connected to a downstream end of a respirator conduit having an open upstream end; supplying a continuous and uninterrupted flow of respiratory gas to a patient from a first location during both inhalation and exhalation phases; feeding pulsed driving gas through a driving gas conduit and out of a jet nozzle 11 located in the respirator conduit and directed toward the downstream end of the respirator from a second location at least one tidal volume upstream of the first location against respiratory gas in the respirator conduit during an inhalation phase to cause the driving gas therein to function as a pneumatic piston to force at least one tidal volume of the respiratory gas from the conduit 5 into the patient's lungs; and causing, during an exhalation phase, expired gas from the patient duct to be fed out through the open upstream end of the respirator conduit.

In this way, respiratory gas introduced at low pressure into the respirator conduit is driven cyclically at any controlled frequency and tidal volume into the patient duct in an inhalation phase of respiration, the driving gas not taking part in gas exchange, and allowing an exhalation phase of respiration to take place between the successive driving pulses.

The principle underlying the invention is thus to use a single respirator tube or conduit and to introduce respiratory gas near or in the patient's airway, while pulses of driving gas introduced into a distal part of the tube having at least one tidal volume, drives the respiratory gas into the patient's lungs. The driving gas is independent of the respiratory gas used for patient ventilation. The use of pulses of driving gases means that there are no valves, pistons or other obstruction in the patient's breathing circuit which may therefore remain open to the atmosphere at all times.

The second location at which the driving gas is introduced into the respirator conduit is spaced sufficiently far upstream of the location at which the respiratory gas is introduced, so that no driving gas takes part in the ventilation of the patient's lungs. Desirably, the first and second locations are spaced apart by a distance such that the volume of the respirator conduit between the two locations is of the order of the average tidal volume involved in respiration.

In one form of the present invention, the respiratory gas is introduced to the respirator conduit via a line which is connected to the respirator conduit adjacent the downstream end of the conduit. However, it is equally possible to introduce a respiratory gas line into the interior of the respirator conduit at a point remote from the downstream end of the conduit and to run the line inside the conduit so that an open outlet end of the gas line is positioned adjacent the downstream end of the respirator conduit. Alternatively, the open outlet end of the gas line may be positioned in the patient duct or extend therefrom so as to be introduced into the patient's airway and be located near the carina in use. The respirator gas line may branch to provide two subsidiary respiratory gas lines each having an outlet for introduction into a respective one of the main bronchi of the lungs of the patient.

Conveniently, the respiratory gas may be derived from a source of compressed breathable gas which may be further admixed with another breathable gas and fed to the respiratory gas line. If desired, various other items may be included in the respiratory gas supply, such as for example a humidifier, a device for introducing anaesthetic gas into the respiratory gas and means for monitoring the condition of the respiratory gas.

The driving gas may be any available pressurised gas (such as compressed air, oxygen or nitrogen) fed via a chopper device to a driving gas line extending through the wall of the respirator conduit and terminating in an axially extending nozzle directed towards the downstream end of the respirator conduit. Desirably, a pressure regulator is included between the connection to the compressed air supply and the chopper device to control the driving pressure to the nozzle and hence the tidal volume, i.e. the ventilating volume to the patient. The chopper device for chopping the driving gas at different frequencies and fixed or variable inspiratory to expiratory time ratios could be mechanical, electronic or pneumatic in nature.

Advantageously, a bypass line is provided around the chopper device and includes a regulator via which a constant stream of compressed air may be supplied to the driving gas nozzle for operation of the respirator in the so-called positive end expiratory pressure (PEEP) mode. Alternatively, an additional nozzle may be provided for this purpose. Further, the bypass may communicate with a second driving gas line which extends into the respirator conduit and terminates in a second driving gas nozzle which is directed axially away from the downstream end of the respirator conduit, so that driving gas can be supplied to this second nozzle for operation of the respirator in the so-called negative end expiratory pressure (NEEP) mode.

BRIEF DESCRIPTION OF THE DRAWINGS

In order that the invention may be readily understood, embodiments thereof will now be described, by way of example, with reference to the accompanying drawings, in which:

FIG. 1 is a diagrammatic representation of part of a respirator embodying the invention, illustrating the principle of operation of a respirator in accordance with the invention;

FIG. 2 illustrates a possible modification of the respirator illustrated in FIG. 1;

DESCRIPTION OF PREFERRED EMBODIMENT

Figure 3:
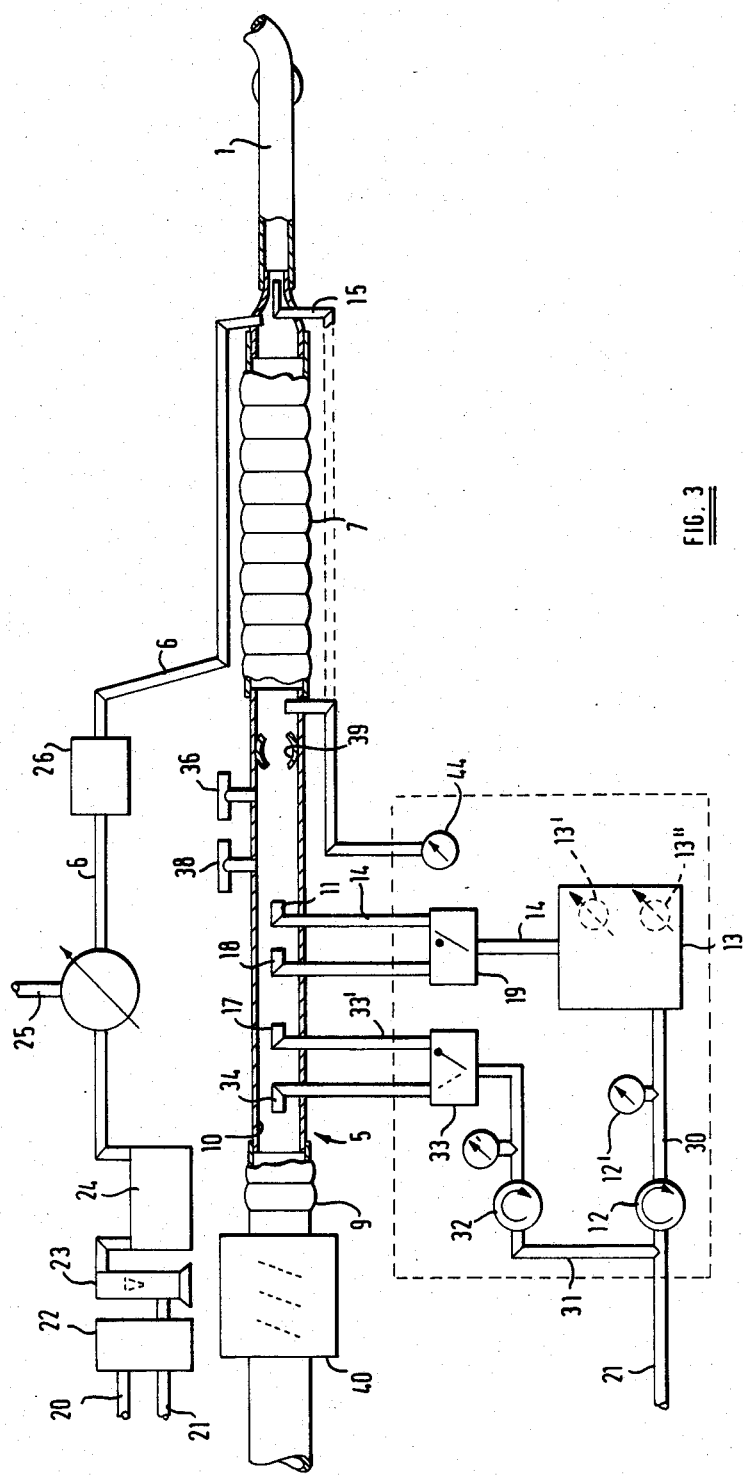
FIG. 3 is a block diagram illustrating the overall structure and connections of a respirator embodying the invention.

Referring firstly to FIG. 1, there is shown a patient duct 1 in the form of a flexible tube for insertion by its distal end 2 into the trachea of a patient. The patient tube 1 has a proximal end 3 to which is attached a downstream end 4 of a flexible respirator conduit 5. A respiratory gas line 6 is connected to a downstream section 7 of the respirator conduit, the line 6 being connected to the conduit 5 adjacent its downstream end 4 and opening into the conduit. The line 6 is connectable via a flow meter 8 to any suitable source of pressurised respiratory gas.

The downstream section 7 of the respirator conduit 5 is connected to an upstream section 9 of the conduit 5 by an intermediate conduit section 10 in which an axially extending driving gas nozzle 11 is supported so as to be directed towards the downstream end of the conduit 5. Nozzle 11 is supplied with a driving gas, such as compressed air, via a pressure regulator 12 and a chopper device 13 which delivers pulses of driving gas to the nozzle 11 via outlet line 14. The supplied pressure is measured by a gauge 12'. The operating frequency of the chopper device 13 is variable by control knob 13' so that the frequency of the driving gas pulses supplied to nozzle 11 can be varied correspondingly.

An airway pressure pipe 15 provided at the downstream end of the respirator conduit extends into the patient duct 1 and is connected to an airway pressure measuring and alarm device (not shown) for monitoring the pressure in the patient duct 1.

FIG. 2 illustrates a modification of the respirator of FIG. 1, whereby the respiratory gas pipe 6 is introduced into the respirator conduit at a point remote from the downstream end 4 and extends along the respirator conduit so that an open outlet end 16 of the respiratory gas pipe is located adjacent the downstream end of the respirator conduit.

Figure 4:
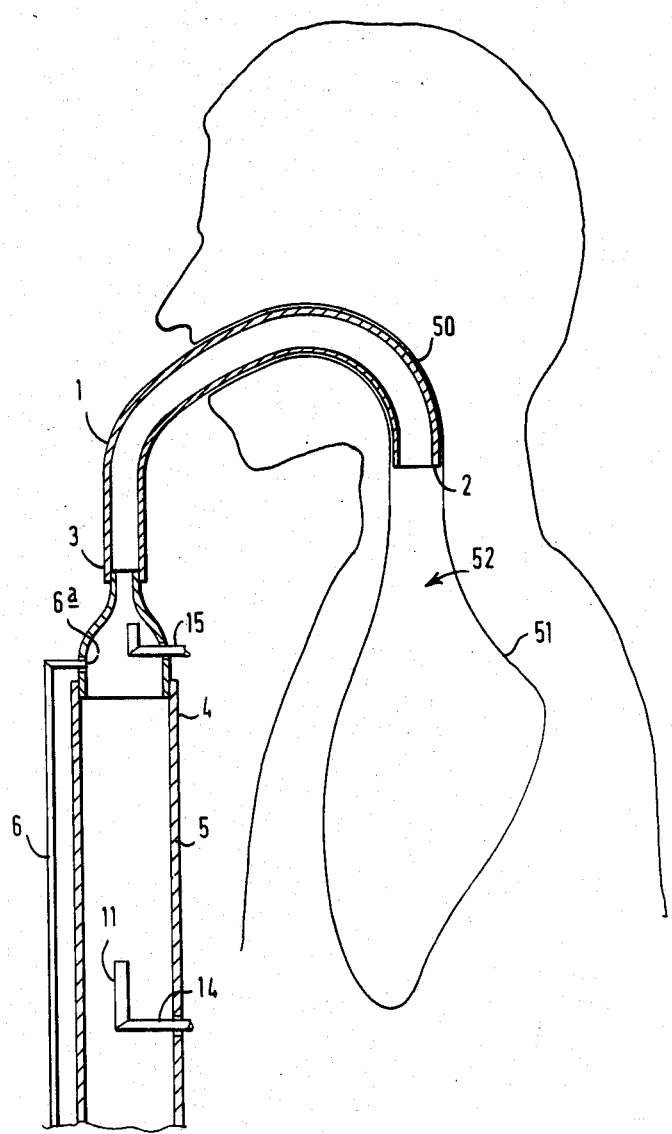
FIGS. 4 and 5 illustrate diagrammatically the use of the respirators shown in FIGS. 1 and 2, respectively, to ventilate a patient.
Figure 5:
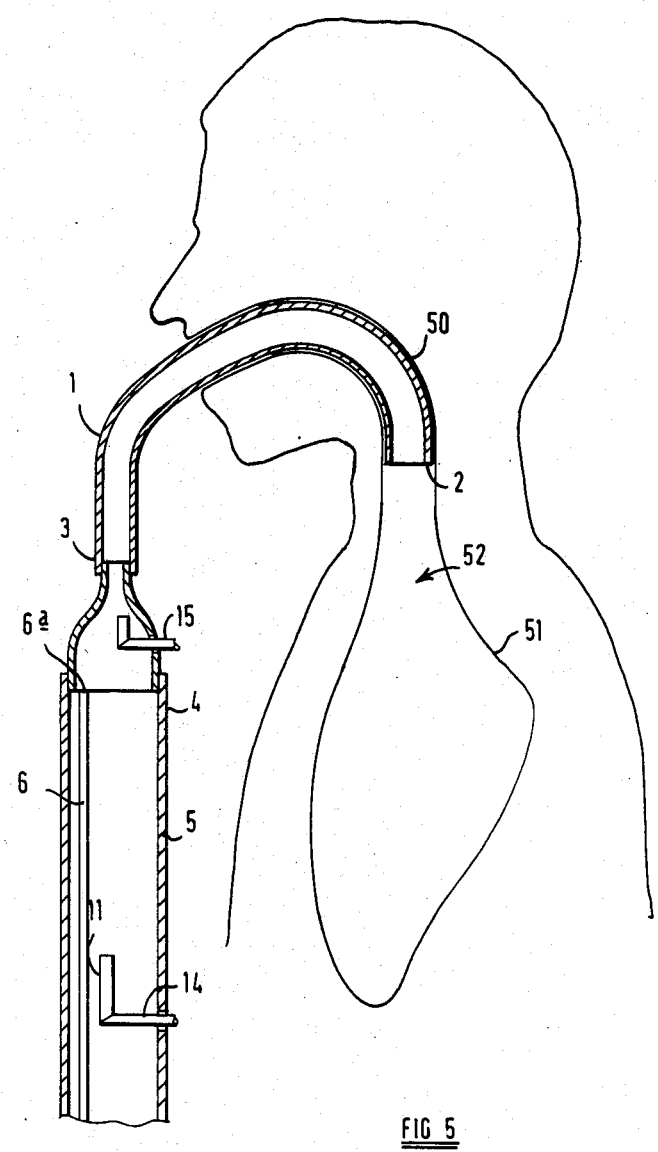

In operation of the respirator illustrated in FIGS. 1 and 2, as shown schematically in FIGS. 4 and 5, respectively, the patient duct 1 is inserted into a patients airway 50 and, respiratory gas is supplied to the line 6 continuously and pulses of driving gas are supplied to the nozzle 11 at a frequency determined by the chopper device 13. The result is that respiratory gas supplied into the downstream end of the respirator conduit is driven into the patient duct and thence into the patient's lungs 51 during an inhalation phase of respiration corresponding to the high pressure pulse of driving gas. Thus, although there is no direct contact between the respiratory gas and the driving gas, it is believed that the column of driving gas in the respirator conduit between the nozzle 11 and the respiratory gas introduced into the downstream end of the conduit serves as a pneumatic piston so that the driving gas acts to force the supplied respiratory gas into the patient duct and the patient's lungs. During an exhalation phase of respiration, corresponding to the interval between pulses of high pressure driving gas, expired gas passes through the patient duct into the respirator conduit past the nozzle 11 into the upstream section 9 of the conduit, from whence it passes to atmosphere or to a scavenging or recovery system. The frequency of respiration can be simply controlled by varying the frequency of the chopper devide 13 and the tidal volume of respiration gas by adjusting the pressure regulator 12.

FIG. 3 shows a more complete respirator arrangement having facilities for varying the constitution of the respiratory gas, for monitoring and treating the gas flow in the respirator duct and for providing different operating modes corresponding to different conditions and requirements of the patient.

In the FIG. 3 embodiment, parts of the respirator corresponds to similar parts in FIGS. 1 and 2 have been given the same reference numerals and the present description will be concerned simply with the additional or modified features of the FIG. 3 respirator.

By way of example, the FIG. 3 respirator is shown as operating with a respiratory gas consisting of a mixture of oxygen obtained from a compressed oxygen line 20 and air obtained from a compressed air line 21. The two constituents of the respiratory gas are mixed in a mixer 22 capable of providing between 21% and 100% oxygen or air. The respiratory gas mixture from the mixer 22 passes via a flow meter 23 to a humidifier 24 in which the humidity of the respiratory gas is optimised, if so desired. The respiratory gas then passes to the respiratory gas line 6. Alternatively, anaesthetic or other gas may be supplied directly to the respiratory gas line 6 from a line 25. Means 26 may be provided to monitor the respiratory gas supplied to line 6 and to give an alarm if the flow, composition or temperature of the respiratory gas is incorrect.

As in the case of FIGS. 1 and 2, a driving gas nozzle 11 is provided in an intermediate section 10 of the respirator conduit 5. The driving gas, which could be any compressed gas, is conveniently compressed air supplied from the line 21 via regulator 12 which controls the driving pressure to the nozzle 11 and hence the tidal volume delivered to the patient. The driving gas delivered by the regulator 12 is supplied to a manifold line 30 which feeds the chopper device 13 adapted to supply pulses of driving gas to nozzle 11 through output line 14. The chopper device 13 is designed to provide a variable frequency from zero to a predetermined maximum to vary the respiration frequency and also a variable mark/space ratio to vary the ratio of inspiration time to expiration time, the latter being adjusted via control knob 13".

A branch line 31 extends from the line 21 via a regulator 32 and a switching device 33 to a line 33' adapted to supply unchopped driving gas directly to a second nozzle 17, so as to provide, if required, operation of the respirator with positive end expiratory pressure (operation in the PEEP mode). Alternatively, it would be possible to incorporate a PEEP valve downstream of the driving jet 11 to provide positive end respiratory pressure PEEP to the patient without using the PEEP jet 17. A third axially extending driving gas nozzle 34 is also provided in the intermediate section of the respirator conduit 5, the nozzle 34 being located upstream of the first nozzle 11 and being directed towards the upstream section of the respirator conduit. This third nozzle 34 can be selectively supplied with driving gas via switching device 33 so as to enable operation of the respirator with negative end expiratory pressure (operation in the NEEP mode).

The maximum pressure which can be generated by a nozzle in the respirator conduit depends upon the driving gas flow and the resistance to back flow of the circuit, i.e. it depends upon the driving pressure and flow resistance of the nozzle system and the diameter and length of the downstream conduit 9.

In order to provide a higher driving pressure for patients with low compliance, a fourth nozzle 18 is provided. This has a wider bore than nozzle 11 and hence, for the same driving gas pressure in line 14 creates a higher pressure in the respirator conduit 7 and thus in the patient duct 1. This "overdrive" nozzle 18 can only be brought into operation by means of a switch 19 which is arranged to return automatically to its position for supplying the driving gas to nozzle 11 when the respirator is switched off.

A manual inflation facility is provided for safe manual operation in the event of a failure of the driving gas system. This facility includes a means 38 for intermittently manually blocking the respirator conduit in any of the sections 7, 10 or 9. Desirably, however, the means 38 is disposed between the driving gas nozzles and the respiratory gas line 6. For safety, a pressure relief valve 36 is incorporated in the respiratory conduit between the respiratory gas line 6 and the occluding means 38 and operates at a predetermined pressure.

As an alternative to blocking the respiratory conduit by a mechanical device, a bag or other means of manual ventilation can be attached at the downstream end of the respirator conduit 5. Such mechanical manual ventilation can readily be instituted with or without stopping the ventilating jet.

A one-way volume meter 39 is provided to monitor the tidal flow of gas in the respirator conduit and may provide an alarm if the supply of a predetermined minimum volume to the patient is not achieved.

In normal operation the upstream section 9 of the respirator conduit may contain a muffler 40 to reduce the noise from the driving gas nozzle. A convenient muffling device would be a low resistance bacterial filter.

FIG. 3 also shows schematically an airway pressure monitoring and alarm device 44 which may be set to give an alarm upon detecting a pressure outside given upper and lower limits. Means may also be provided for monitoring the carbon dioxide content of the expired gas at the end of the tidal flow. Also a carbon dioxide absorption system could be incorporated in the respirator conduit 5 to reduce the respiratory fresh gas requirement. As regards adaptation to the condition of the patient, it is envisaged that a servo control may be provided for adjusting the pressure of the driving gas to maintain a set tidal volume in the face of changing airway resistance and thoracic compliance. The respirator may also monitor its electrical supply so as to give an alarm if the supply should fail and, in the case of electrically driven chopper, change the chopper over automatically to operation by a backup battery.

Whilst the present respirator requires a supply of compressed air or other gas at relatively high pressure, for example, 60 p.s.i. (4 bars) for use as the driving gas, this is routinely provided in any modern hospital theatre or intensive care unit.

When the fresh respiratory gas used is 100% oxygen after washout of lung nitrogen, apnoeic oxygenation can be instituted merely be stopping the driving jet 11 while maintaining the oxygen fresh gas supply at any point of the breathing circuit ie, patient duct, airways or respirator conduit.

Fresh respiratory gas can be supplied at different flow rates and at different sites in patient's airways or patient duct, that is upstream of the more usual connection at the junction of the patient duct and the respirator conduit 5 shown in FIGS. 1 to 3. The respiratory gas line 6 may comprise one of various catheters or tubes of various diameters placed either independently in the patient's airway or as part of the patient duct so that the respiratory gas outlet 6a of the respiratory gas line 6, that is the tip, distal orifice(s) or side hole(s) of one or more catheters, are placed: (a) at any point along the patient duct 1; (b) near the carina, that is the bifurcation of the main airway (the trachea) into the two main bronchi; or (c) in the bronchi.

In this way the patient duct can be scavenged wholly, or in part, of alveolar stale gas with respiratory fresh gas.

Artificial ventilation is, of course, applied by the driving jet in the manner described above.

When the fresh respiratory gas used is 100% oxygen, after washout of lung nitrogen, apnoeic oxygenation (mass transfer of oxygen) can be instituted merely by stopping the driving jet 11 while maintaining the oxygen fresh gas supply at any point of the breathing circuit ie, patient duct, airway or respirator conduit.

Figure 6:
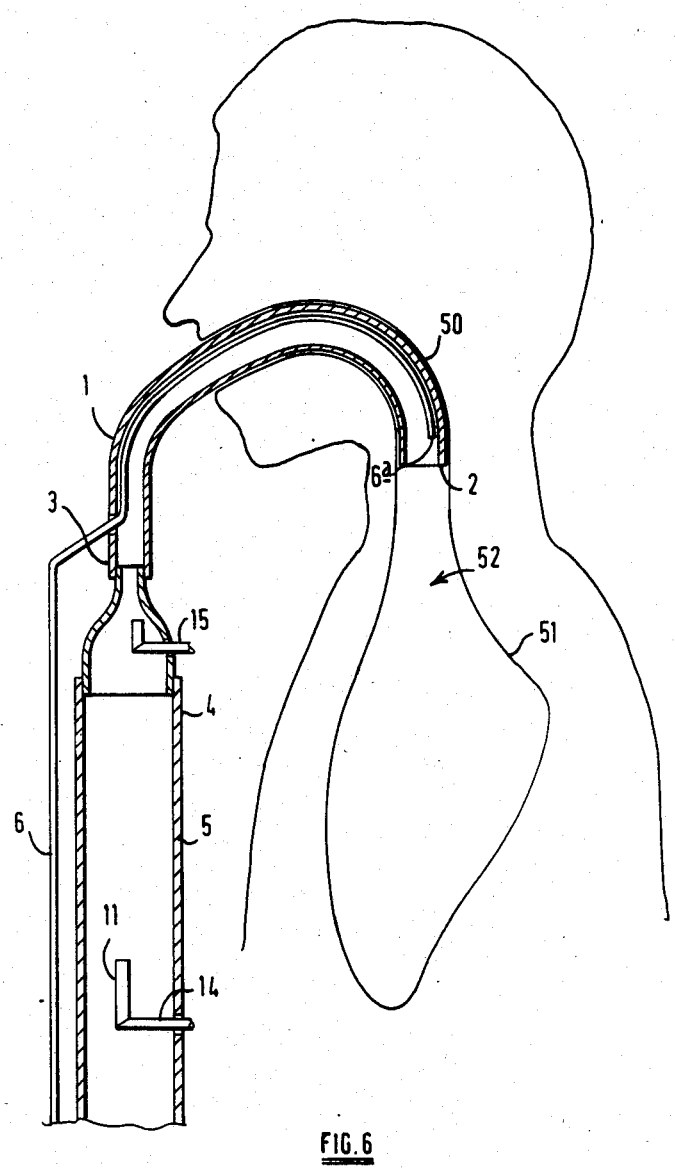
FIGS. 6 to 8 illustrate diagrammatically the use of various further modified forms of the respirator to ventilate a patient.
Figure 7:
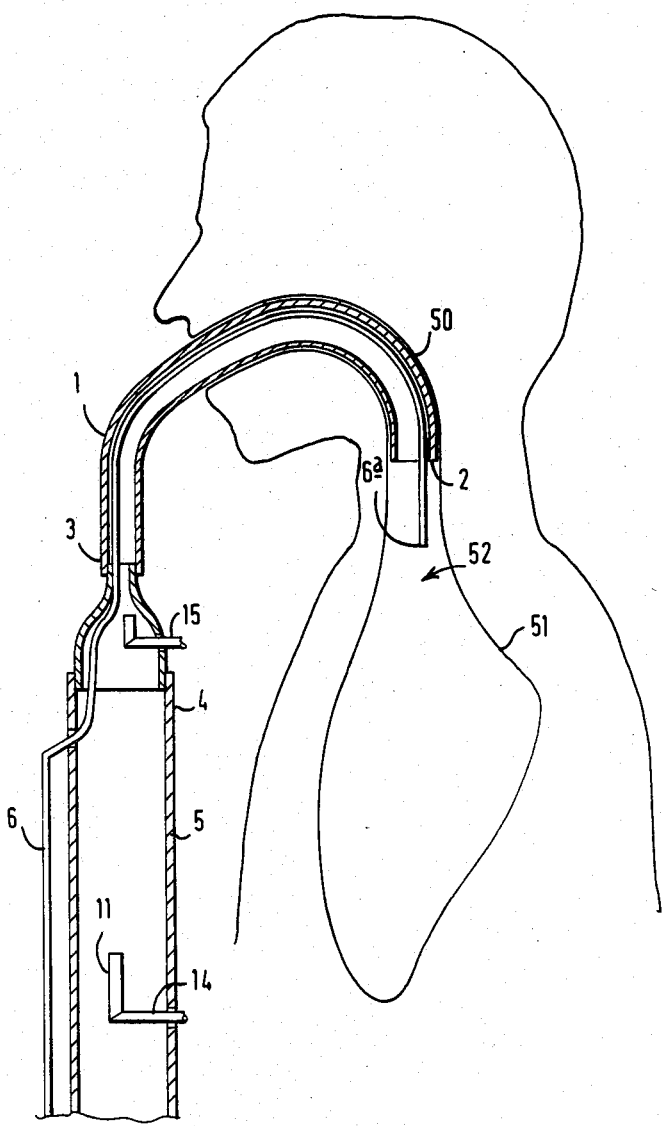
Figure 8:
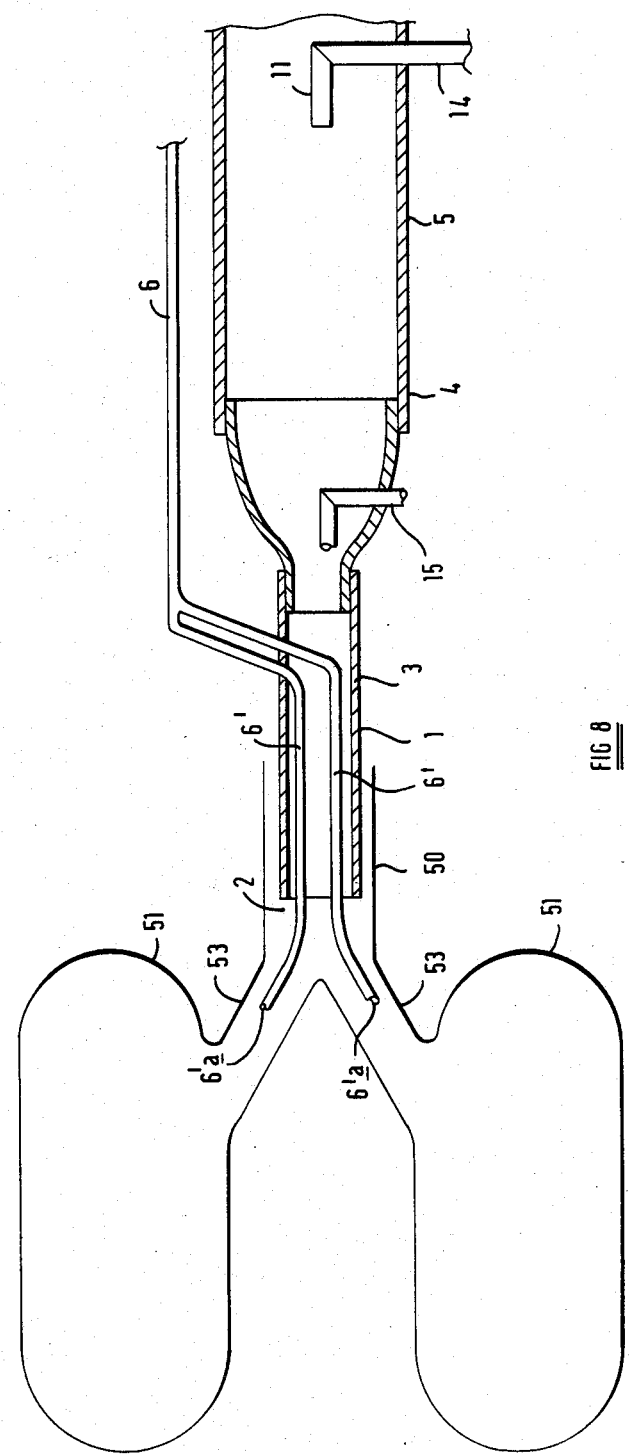

FIGS. 6 to 8 illustrate various modifications of the respirator of FIGS. 1 to 2 or 3 to place the respirator gas outlet at various different positions upstream of the position shown in FIGS. 1 to 3 and to show the positioning of the patient duct 1 in the patients airway 50 during use of the respirator.

As shown in FIG. 6, the respiratory gas line 6 enters the patient duct 1 at the upstream section 3 thereof and extends along the patient duct to terminate just before the upstream or distal end 2 of the patient duct 1 so that respiratory gas is supplied via the outlet 6a at a first location just upstream of the distal end 2 of the patient duct 1. Of course, the respiratory gas line 6 may terminate at any location along the patient duct 1 and the outlet 6a need not necessarily be at the end thereof but could be in the form of one or more side opening.

In the arrangement shown in FIG. 7, the respiratory gas line 6 enters the respirator conduit 5 adjacent the end 4 thereof and extends through the patient duct 1 beyond the distal end 2 thereof to terminate, when the patient duct 1 is inserted into a patients airway as shown, near the carina 52 of the patient so that the fresh respiratory gas outlet 6a is positioned at or near the carina.

FIG. 8 illustrates schematically the lungs 51 of a patient into whose airway 50 the patient duct 1 of a further modified respirator has been introduced. In the arrangement shown in FIG. 8, the respiratory gas line 6 bifurcates to form two subsidiary respiratory gas lines 6' each of which enters the patient duct 1 near the proximal end 3 thereof and extends along the patient duct beyond the distal end 2 thereof so that, when the patient duct 1 is inserted into a patient's airway as shown, the outlet 6'a of each subsidiary respiratory gas line 6' extends into a respective one of the two main bronchi 53 of the patient.

Of course, various combinations of the modifications shown in FIGS. 6 to 8 are possible.

The operation of the modified respirators shown in FIGS. 6 to 8 is substantially identical to that of the respirators previously described herein. The respirators described hereinbefore have numerous advantages in construction and operation. For example, the fact that there is no valve in the patient's circuit means that the patient is capable of breathing spontaneously during any period of ventilation and there is no need to synchronise the operation of the respirator with spontaneous breathing effort. Furthermore, a patient connected to the respirator can be reversed from the effect of paralysing drugs without disconnection from the respirator. The respirators provide for simple and immediate change-over to continuous positive airway pressure (CPAP) ventilation without disconnecting the respirator and, in contrast to known respirators having end expiratory pressure control, provide for simple operation in this mode without requiring valves. Thus it is suitable for weaning patients from aritifical ventilation, either with CPAP or intermittent mandatory ventilation.

The respirator is also capable of normal to high frequency operation by simply changing the chopping frequency without changing any other settings. Thus, the ventilator can provide large to vary small tidal volmes (down to zero) and as the humidifier is not included in the patient's beathing circuit, it is suitable for any age group, since the size of the respiratory conduit can be selected to match the appropriate tidal volume.

The characteristics of the driving gas arrangement are such that the respirator may be safely connected to any patient from adult to neonate at any setting of the ventilator and the normal minute volume of inspired respiratory gas is adequate at all frequencies of controlled ventilation. The described respirator also provides for simple manual ventilation of the patient without any need to disconnect the respirator. Whilst a safety release valve is provided in the described embodiment of the invention, this is merely provided for safety when using manual inflation and is unnecessary normally, as the patient circuit is open to atmosphere.

As far as the supply of respiratory gas is concerned, any respiratory gas concentration and anaesthetic gases can be used without requiring any complicated changes in the circuit. In operation, the present respirator requires minute volumes comparable to known respirators, other than the known jet respirators which require considerable compensating adjustment and very high respiratory rates. The described respirator also enables the respiratory gas to be humidified in a simple fashion.

The structure of the described respirator is such that very simple disposal or autoclavable patient tubing can be employed, together with a simple and easily cleaned respirator conduit. The resulting respirator provides a small and compact machine at low cost with a simple and straightforward operation which does not require special training of operators. The simple respirator conduit construction can provide effective antipolution scavenging and operation with an acceptable noise level.

Thus, respirators for use in replacing or assisting the respiratory function in patients in whom spontaneous respiration is either absent or insufficient are described. Each respirator includes a respirator conduit having a downstream end which is attachable to a proximal end of a patient tube 3. A respiratory gas line 6 is connected to a downstream section of the conduit and opens into the conduit at a first location adjacent but upstream of the downstream end 4. An axially extending driving gas jet nozzle 11 is provided at a location which is at least one tidal volume upstream from the patient attachment, where the respiratory fresh gas is supplied. The driving gas from the driving jet 11 simply controls the tidal volume like a pneumatic piston and drives the respiratory gas accumulated in the conduit 5 from the supply of the continuous flow of the respiratory gas. The driving gas from jet 11 does not take part in the pulmonary gas exchange. Ventilation of any patient at any frequency and tidal volume is possible with this new respirator, safely, with any chosen low pressure conditioned and humidified respiratory gas including volatile anaesthetic vapours.

In its simplest form the respirator can be described as a slave driving jet placed in the wide tube of a T-piece, one tidal volume distal to the patient attachment where the respiratory gas is supplied through the narrow limb of the T-piece.

Although a particular embodiment of the invention has been described and illustrated herein, it is recognised that modifications may readily occur to those skilled in the art and consequently it is intended that the following claims be interpreted to cover such modifications and equivalents.

What is claimed is:

1. A respirator including a respirator conduit having a downstream end for connection to a patient duct;
   supplying means for supplying relatively low pressure respiratory gas to a patient through and out of the patient duct;
   the respiratory gas supplying means comprising a respiratory gas line having a first end for connection to a respiratory gas supply, the respiratory gas line being divided at a point remote from the first end thereof to form two subsidiary respiratory gas lines each having a respective end, the end of each subsidiary respiratory gas line extending beyond the patient duct for location in a respective one of the main bronchi of the patient;
   means for introducing and directing pulses of driving gas axially of and in the respirator conduit towards the downstream end of the respirator conduit from upstream of the respiratory gas supplied by the supplying means to drive the respiratory gas into a patient's lungs; and
   means for supplying a constant stream of driving gas to the respirator conduit for operation with a desired end expiratory pressure.

2. A method of ventilating a patient, comprising:
   inserting one end of a patient duct into the mouth of the patient;
   attaching a respirator conduit to the patient duct;
   continuously supplying relatively low pressure respiratory gas to the patient downstream of the patient duct;
   introducing pulses of driving gas into a respirator conduit directed toward the downstream end of the respirator conduit connected to the patient duct to drive the respiratory gas directly into the patients bronchi.

* * * * *